United States Patent
Lin Charna

(10) Patent No.: US 10,517,511 B2
(45) Date of Patent: Dec. 31, 2019

(54) PATIENT OFF-BED NOTIFICATION SYSTEM

(71) Applicant: Sharon Lin Charna, Irvine, CA (US)

(72) Inventor: Sharon Lin Charna, Irvine, CA (US)

(73) Assignee: Hello Nurse Medical Innovations, Inc., Irvine, CA (US)

( * ) Notice: Subject to any disclaimer, the term of this patent is extended or adjusted under 35 U.S.C. 154(b) by 0 days.

(21) Appl. No.: 16/006,898

(22) Filed: Jun. 13, 2018

(65) Prior Publication Data

US 2018/0360348 A1 Dec. 20, 2018

Related U.S. Application Data

(60) Provisional application No. 62/524,860, filed on Jun. 26, 2017.

(30) Foreign Application Priority Data

Jun. 14, 2017 (TW) .............................. 106208622 U
Jul. 28, 2017 (TW) .............................. 106211104 U

(51) Int. Cl.
*A61B 5/11* (2006.01)
*A61B 5/00* (2006.01)

(52) U.S. Cl.
CPC .......... *A61B 5/1115* (2013.01); *A61B 5/0004* (2013.01); *A61B 5/6892* (2013.01);
(Continued)

(58) Field of Classification Search
CPC ... A61B 5/1115; A61B 5/0004; A61B 5/6892; A61B 5/7405; A61B 5/742;
(Continued)

(56) References Cited

U.S. PATENT DOCUMENTS

| | | | |
|---|---|---|---|
| 8,672,842 B2 * | 3/2014 | Kenalty | A61B 5/0015 324/691 |
| 2007/0040692 A1 * | 2/2007 | Smith | A61B 5/1115 340/573.1 |

(Continued)

FOREIGN PATENT DOCUMENTS

JP 05115341 A * 5/1993

*Primary Examiner* — Hirdepal Singh
(74) *Attorney, Agent, or Firm* — J.H. Lin Patent Law P.C.; John H. Lin

(57) ABSTRACT

The present invention relates to a patient off-bed notification system, which includes a pressure-sensitive sensor pad, a signal converter, and a signal transmitter. The pressure-sensitive sensor pad includes an upper conductive layer, a bottom conductive layer, and an insulating layer arranged therebetween, where the upper conductive layer and the bottom conductive layer can generate an electrical signal due to a pressure change. The signal converter is used to receive the electrical signal from the pressure-sensitive sensor pad and perform operational analysis to produce a corresponding patient status signal. The signal transmitter transmits the patient status signal from the signal converter to a server, and the server displays or/and stores corresponding information according to the patient status signal. Thus, patient's statuses in bed can be known at any time, and the harm caused when the patient leaves the bed alone can be minimized, thus effectively improving the work efficiency of caregivers.

12 Claims, 7 Drawing Sheets

(52) U.S. Cl.
CPC ............ *A61B 5/742* (2013.01); *A61B 5/7405* (2013.01); *A61B 5/746* (2013.01); *A61B 5/7455* (2013.01); *A61B 2562/0247* (2013.01); *A61B 2562/046* (2013.01)

(58) Field of Classification Search
CPC .................. A61B 5/7455; A61B 5/746; A61B 2562/0247; A61B 2562/046; G01C 21/367; G06T 11/203; G09G 5/026; G08B 21/02
USPC ...................................................... 340/573.4
See application file for complete search history.

(56) References Cited

U.S. PATENT DOCUMENTS

| | | | | |
|---|---|---|---|---|
| 2016/0007887 | A1* | 1/2016 | Shimizu | A61B 5/1115 340/573.4 |
| 2017/0089775 | A1* | 3/2017 | Hsu | G01L 1/16 |
| 2017/0224253 | A1* | 8/2017 | Berlin | A61B 5/1115 |
| 2017/0236398 | A1* | 8/2017 | Eddy | A61B 5/6892 340/573.5 |
| 2019/0049322 | A1* | 2/2019 | James | A61B 5/6892 |
| 2019/0051137 | A1* | 2/2019 | Kilcran | A61B 5/0022 |

* cited by examiner

PATIENT OFF-BED NOTIFICATION SYSTEM

CROSS REFERENCE TO RELATED APPLICATIONS

The present application claims the benefit of U.S. provisional patent application No. 62/524,860 filed on Jun. 26, 2017, Taiwanese patent application No. 106208622 filed on Jun. 14, 2017, and Taiwanese patent application No. 106211104 filed on Jul. 28, 2017. All the above are hereby incorporated by reference.

BACKGROUND OF THE INVENTION

Technical Field

The present invention wholly relates to the technical field of medical care facilities, and in particular, to a notification system that can be laid flat on a proper position of a sickbed to know patient's statuses in the bed at any time by the body weight of a patient; and to predict and judge, according to the patient's statuses in the bed, whether the patient intends to get out of bed.

Background

As medical techniques and technologies dramatically develop, human lifespan is prolonged a lot. However, while the lifespan is prolonged, the chance of illness increases a lot accordingly. Although modern medicine can overcome most diseases and gives patients a healthy body, the patients must eventually undergo a medical process before recovering.

In facing relatively serious or complicated illness conditions, some patients have to be on bed rest to receive medical treatment or observation, and definitely, a few patients have difficulty in getting up alone or even are unable to do so. Further, there also exist a minority of patients who are able to take care of themselves but still need assistance or observation from nursing staff or medical staff. Therefore, the workload of the nursing staff or medical staff becomes increasing heavy. Moreover, from the perspective of an increasingly extensive and long-lasting course, use of only technological medical equipment fails to effectively reduce the demands for the number and the workload of the nursing staff.

It has been pointed out by related follow-up study in Taiwan that, the ratio of patients to nurses in Taiwan's regional or above hospitals is 12:1 during the years from 2006 to 2007. Moreover, due to the social pattern characterized by rapid population aging, it can be predicted that there will be increasingly more bedridden patients and the time cost in the sickbed also significantly increases. Therefore, the demands for the number and the workload of nursing staff also significantly grow. During the care of mentally retarded patients who act freely but have confused consciousness, or patients who have physical and mental dysfunction and require caregivers' accompaniment, the caregiver always worries that the patient leaves the sickbed alone or drops from the sickbed to cause accidental damage. When the patient drops from the sickbed or tumbles after leaving the sickbed, an adverse consequence such as severe harm or even death may be incurred if the caregiver fails to immediately handle such situations in the first place.

Taiwan utility model patent (certification NO.: M465634) No. 102207861 that has been published discloses "Protective Alert device for Sickbed", the sickbed having a bed surface for supporting the human body, a front end portion closed to the head of the human body, and a rear end portion closed to the feet. The protective alert device includes: a carrier configured on the sickbed; a light sensitive unit, mounted on the carrier and forming a height difference with the bed surface of the sickbed, and used to receive light rays along a sickbed short-side direction within a sensing range not larger than the length of the sickbed short side; and an alarm unit, electrically connected to the light sensitive unit and used to generate a warning signal when the light rays in the sensing range have a change.

In the foregoing first former invention, limited to the sickbed short-side direction, the sensing range can be extended to the whole sickbed with reduced dead angles, thus achieving a protection effect. However, this former invention cannot sense patient's statuses in bed, and further cannot predict and judge whether the patient intends to get out of bed. When the patient drops from the sickbed or tumbles after leaving the bed, an adverse consequence such as severe harm or even death can be avoided if a caregiver makes prevention in advance.

Taiwan utility model patent (certification NO.: M447769) No. 101219854 that has been published discloses "Sickbed for Sensing Patient's Action of Leaving Bed", where the sickbed includes: a bedstead having at least one off-bed side; a detection module including a plurality of detection units arranged on the bedstead, each detection unit being able to send out a warning signal when sensing that the patient's body passes through the off-bedside; a processing module, connected to the sensing units of the sensing module via a signal and capable of receiving and processing the warning signals sent by the detection units, the processing module further sending out an off-bed signal when simultaneously receiving multiple warning signals; and an alert module, connected to the processing module via a signal and capable of sending out an alert signal when driven by the off-bed signal.

In the foregoing second former invention, the detection units can send out a warning signal when the patient leaves the bed, such that the nursing staff are timely informed and then immediately go to the ward to take care of the patient. However, this former invention cannot sense patient's statuses in bed, and further cannot predict and judge whether the patient intends to get out of bed. When the patient drops from the sickbed or tumbles after leaving the bed, an adverse consequence such as severe harm or even death can be avoided if the caregiver makes prevention in advance.

Therefore, it is necessary to solve the foregoing problems so as to avoid accidents and reduce the manpower, costs, and time. In view of the defects in the prior art, the applicants finally conceive the present invention through careful experimentation and research with perseverance, to overcome the defects in the prior art.

SUMMARY OF THE INVENTION

In view of the problems in the prior art, the present invention provides a patient off-bed notification system, which aims to send out a signal to notify a caregiver before a patient leaves the bed, and continuously send out a notification signal after the patient leaves the bed, so as to remind the caregiver to go to the ward and take care of the patient. Thus, the harm caused when the patient leaves the bed alone can be minimized, thus effectively improving the work efficiency of the caregiver.

According to the objective of the present invention, the present invention provides a patient off-bed notification system, which includes a pressure-sensitive sensor pad, a signal converter, and a signal transmitter. The pressure-sensitive sensor pad includes an upper conductive layer, a bottom conductive layer and an insulating layer arranged therebetween, where the upper conductive layer and the bottom conductive layer can generate an electrical signal due to a pressure change. The signal converter is electrically connected to the pressure-sensitive sensor pad, and is used to receive the electrical signal sent by the pressure-sensitive sensor pad and perform operational analysis to produce a corresponding patient status signal. The signal transmitter is electrically connected to the signal converter and transmits the signal.

According to an implementation manner of the patient off-bed notification system of the present invention, the pressure-sensitive sensor pad can be further divided into at least one or a plurality of pressure-sensitive sensing zones, where the at least one or the plurality of pressure-sensitive sensing zones produces electrical signals due to a foreign force or pressure change, the electrical signals being the same or varying from each other, or some of them being the same.

According to an implementation manner of the patient off-bed notification system of the present invention, the number of the at least one or the plurality of pressure-sensitive sensing zones and their positions are not limited, and can be determined according to sensed pressures and positions. For example, the pressure-sensitive sensor pad is divided into three zones: a left one, a middle one and a right one, and further the middle zone thereof is divided into four sub-zones; in addition, these pressure-sensitive sensing zones have the same or different sensing areas, or some of them have the same sensing areas.

According to an implementation manner of the patient off-bed notification system of the present invention, the insulating layer is provided with multiple pierced regions used to form these pressure-sensitive sensing zones by partitioning.

According to an implementation manner of the patient off-bed notification system of the present invention, the system further includes a server, used to receive the patient status signal sent by the signal transmitter.

According to an implementation manner of the patient off-bed notification system of the present invention, the server further includes a display unit, used to store and/or display information corresponding to the patient status signal, where the display unit is a computer screen or an LED panel. For example, the display unit can display whether the patient is in a normal status or a dangerous status, and also display patient information including the ward number, bed number, patient name, occurrence time of a dangerous condition, and the like.

According to an implementation manner of the patient off-bed notification system of the present invention, the patient off-bed notification system further includes at least one alert device for sending out a warning signal, where the alert device is communicatively connected to the server and used to receive the information corresponding to the patient status signal. When the patient is in a dangerous status, the display unit can display the patient information including the ward number, bed number, patient name, occurrence time of a dangerous condition, and the like; and the alert device can synchronously send out a warning signal.

According to an implementation manner of the patient off-bed notification system of the present invention, the warning signal is presented in at least one of the following manners: sound, an image, vibration, light, and a digital signal.

According to an implementation manner of the patient off-bed notification system of the present invention, the alert device is at least one of a wireless BB call, a mobile phone, a buzzer, an alarm lamp, and an audio alarm; or may also be an alert device having alarm functions of at least two of a buzzer, an alarm lamp, and an audio alarm. For example, the alert device can display different lamp signals and emit warning sound to indicate the status of the patient; or a mobile phone is used to emit warning sound and display patient information including the ward number, bed number, patient name, occurrence time of a dangerous condition, and the like.

According to an implementation manner of the patient off-bed notification system of the present invention, when the patient is in a dangerous status, the alert device can unceasingly send out the warning signal at regular intervals, till the warning is lifted.

According to an implementation manner of the patient off-bed notification system of the present invention, the signal transmitter can transmit a signal via a wireless transmission manner such as WIFI, ZigBee, or Bluetooth.

According to an implementation manner of the patient off-bed notification system of the present invention, the pressure-sensitive sensor pad is arranged in a bed, where the bed further includes an upper cushion and a bottom cushion, and the pressure-sensitive sensor pad can be placed on the upper cushion or between the upper cushion and the bottom cushion.

DESCRIPTION OF NUMERALS IN THE DRAWINGS

Figure 1:
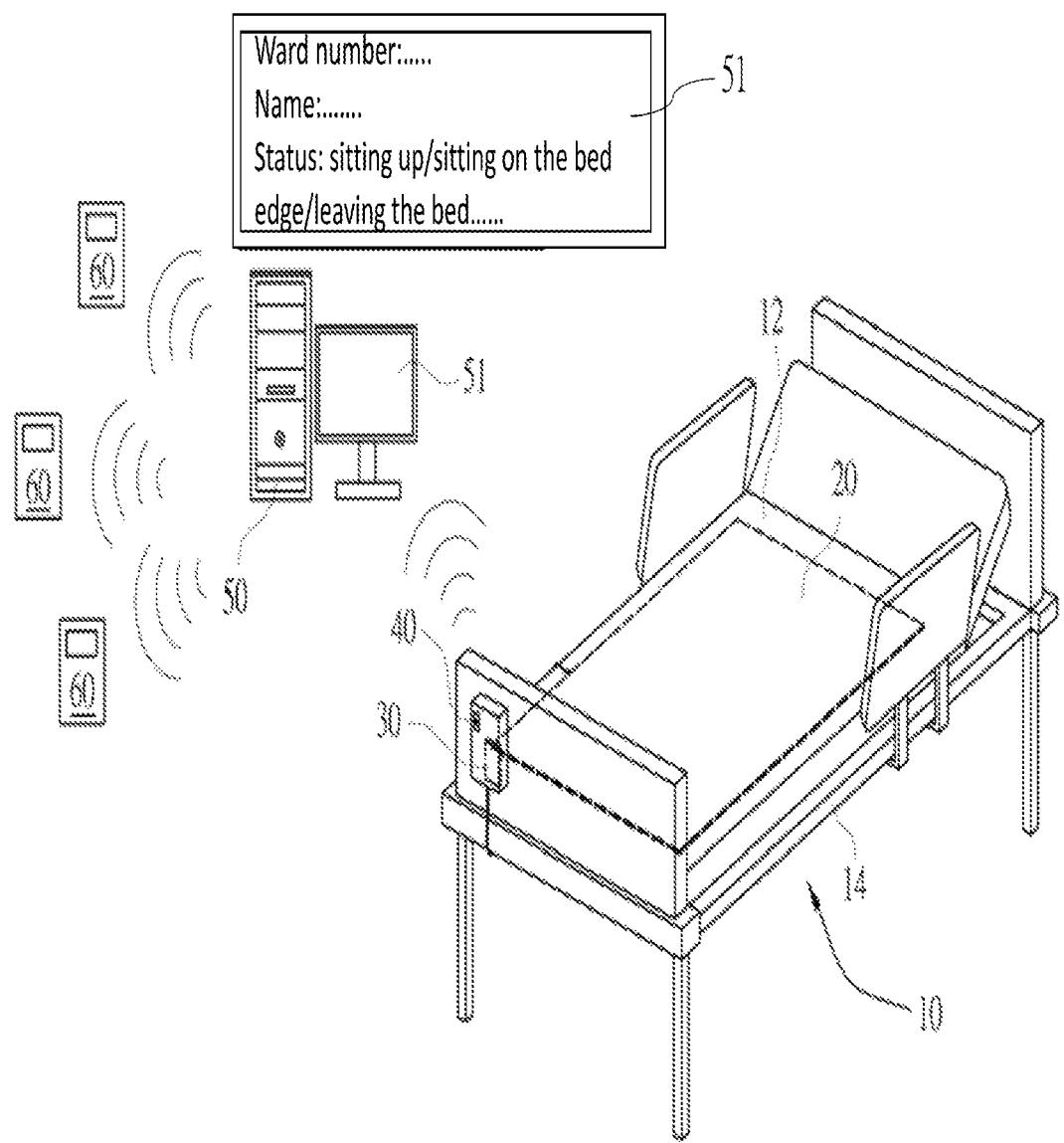
FIG. 1 is a schematic architecture diagram of an embodiment of a patient off-bed notification system according to the present invention.

10 Bed
12 Upper cushion
14 Bottom cushion
20 Pressure-sensitive sensor pad
22 Upper conductive layer
24 Bottom conductive layer
26 Insulating layer
200 Pressure-sensitive sensing zone
200a~200f Pressure-sensitive sensing zones
260 Pierced region
30 Signal converter
40 Signal transmitter
40' Calling device
50 Server
50' monitoring alert apparatus (50')
51 Display unit
60 Alert device
S1~S7 Steps

DETAILED DESCRIPTION OF THE PREFERRED EMBODIMENTS

Technical means used by the present invention to achieve the set invention objectives is further described below with reference to the accompanying drawings and preferred embodiments of the present invention.

Figure 2:
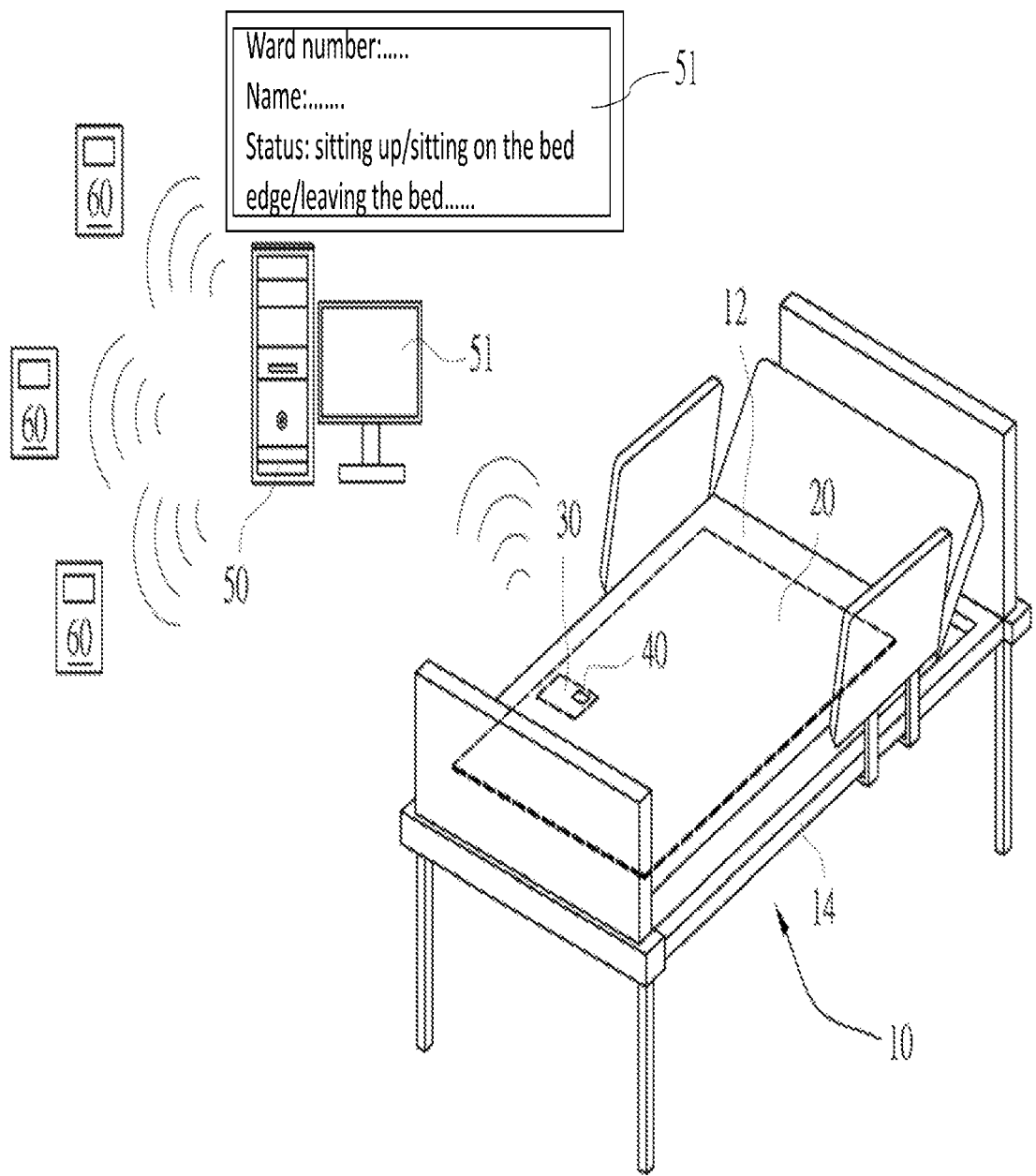
FIG. 2 is a schematic architecture diagram of another embodiment of a patient off-bed notification system according to the present invention.

Refer to FIG. 1 and FIG. 2, which are schematic diagrams respectively showing one embodiment and the other embodiment of an architecture of a patient off-bed notification system of the present invention. The patient off-bed notification system disclosed in the present invention is mainly formed by a pressure-sensitive sensor pad (20), a signal converter (30), and a signal transmitter (40) that are arranged in a bed (10). The bed (10) includes an upper cushion (12) and a bottom cushion (14). The bottom cushion (14) is mainly used as a support, and therefore may be a part of a bedstead (not shown in the figures) in practice. The signal converter (30) and the signal transmitter (40) are arranged outside, and are connected to the pressure-sensitive sensor pad (20) via an information transmission line, as shown in FIG. 1. Alternatively, the signal converter (30) and the signal transmitter (40) are integrated in the pressure-sensitive sensor pad (20), as shown in FIG. 2. The present invention does not limit an arrangement manner thereof.

Figure 3:
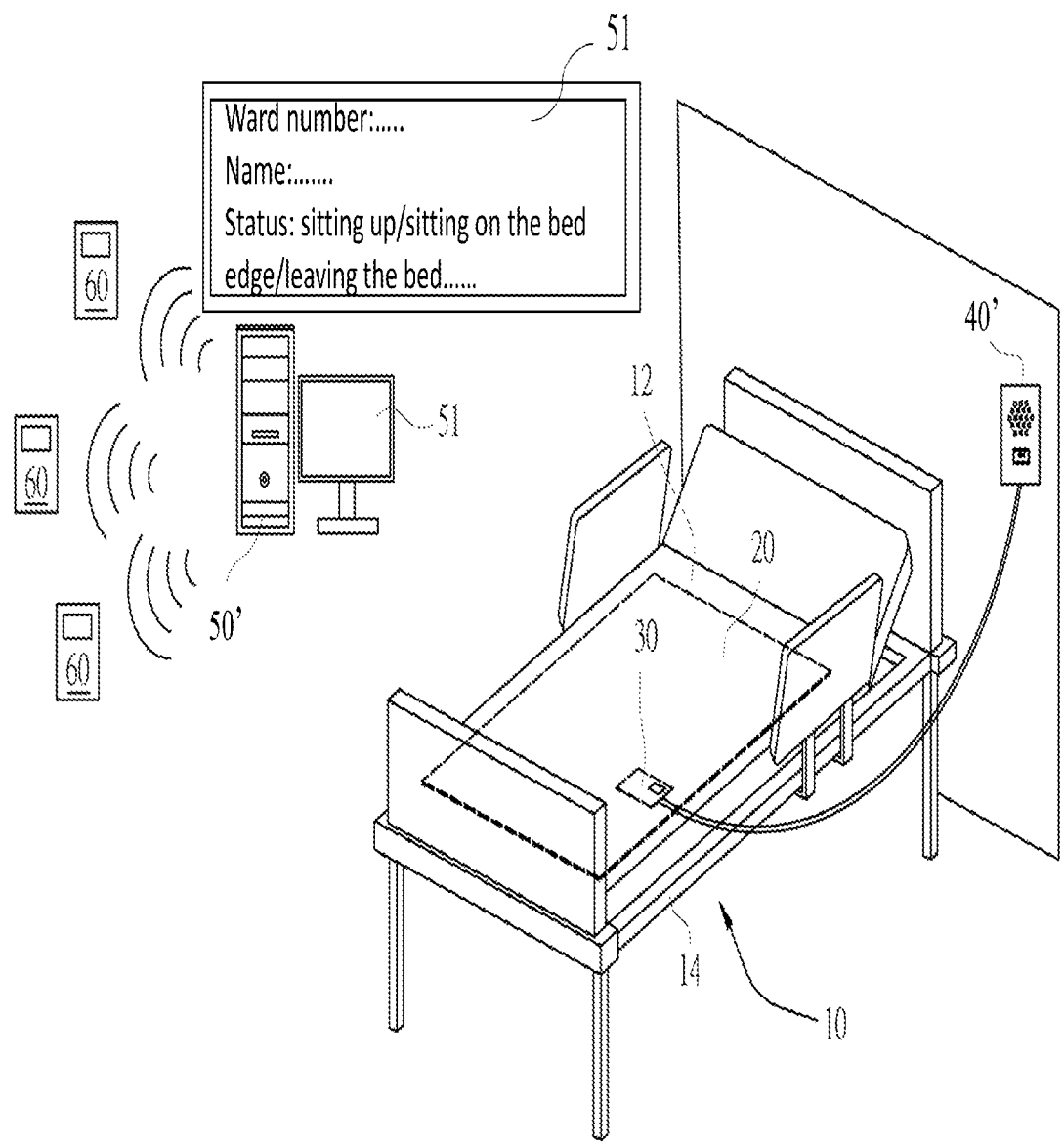
FIG. 3 is a schematic architecture diagram of another embodiment of a patient off-bed notification system according to the present invention.

Furthermore, the patient off-bed notification system of the present invention can also be connected with calling system of the hospital nurse station directly. Refer to FIG. 3, which is schematic diagram showing another embodiment of an architecture of a patient off-bed notification system of the present invention. In the embodiment, the signal transmitter is an existing calling device (40') in the ward, and the server is the monitoring alert apparatus (50') set at the hospital nurse station. The signal converter (30) is electrically connected to the calling device (40') and sends the patient status signal to the monitoring alert apparatus (50') by the calling device (40').

In this embodiment, the calling device (40') is generally installed on the wall surface near the sickbed and usually is the existing one which has been installed in the ward. In addition, the calling device (40') has communication interface can be respectively connected to the signal converter (30) and the monitoring alert apparatus (50') set at the nursing station in a manner of augmenting the communication interface with wire connection or wireless connection. The calling device (40') is provided with an emergency button. When an emergency occurs to the patient, the emergency button can be pressed by the patient to send a warning signal to the monitoring alert apparatus (50'). And when the signal converter (30) is electrically connected to the calling device (40'), the calling device (40') can also sent the patient status signal from the signal converter (30) to the monitoring alert apparatus (50') to notify the nursing staff if the patient is about to leave the bed or is about to fall.

Figure 4:
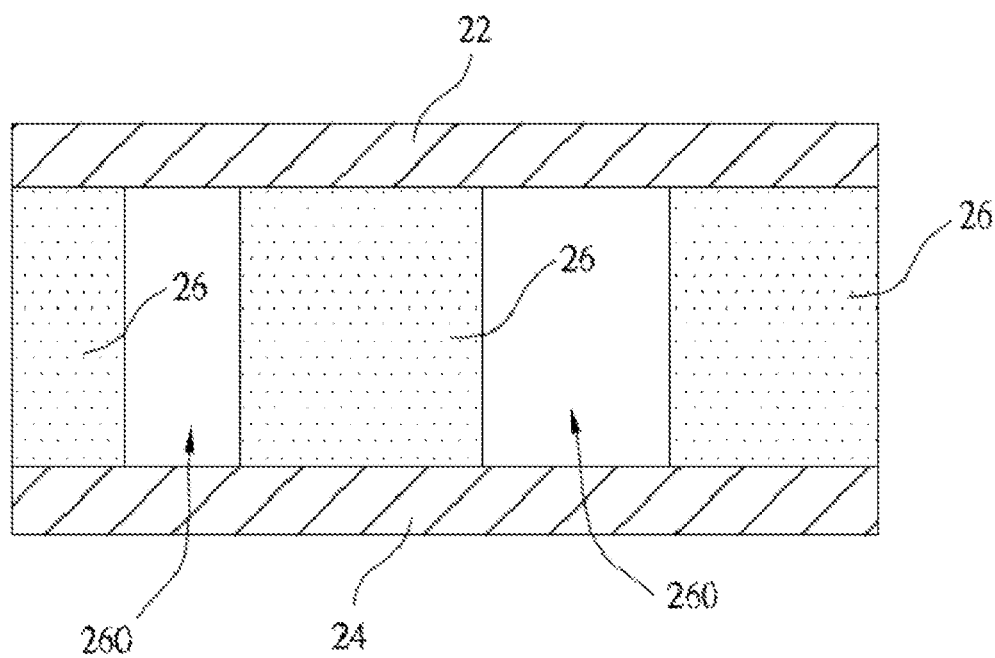
FIG. 4 is a schematic structural diagram of a section of a pressure-sensitive sensor pad according to the present invention.

Refer to FIG. 4, which is a schematic structural diagram of a section of a pressure-sensitive sensor pad according to the present invention. The pressure-sensitive sensor pad (20) is designed into a rectangular sheet according to the shape of the bed (10). The pressure-sensitive sensor pad (20) may be a soft pad formed by an upper conductive layer (22), a bottom conductive layer (24), and an insulating layer (26) arranged therebetween, where three layers are arranged in parallel with each other. The insulating layer (26) is provided with multiple pierced regions (260). These pierced regions (260) partition the upper conductive layer (22) and the bottom conductive layer (24) into multiple pressure-sensitive sensing zones (200). Each pressure-sensitive sensing zone (200) forms a pressure-resistant pressure sensor structure, and these pressure-resistant pressure sensor structures are separately electrically connected to the signal converter (30).

Figure 5:
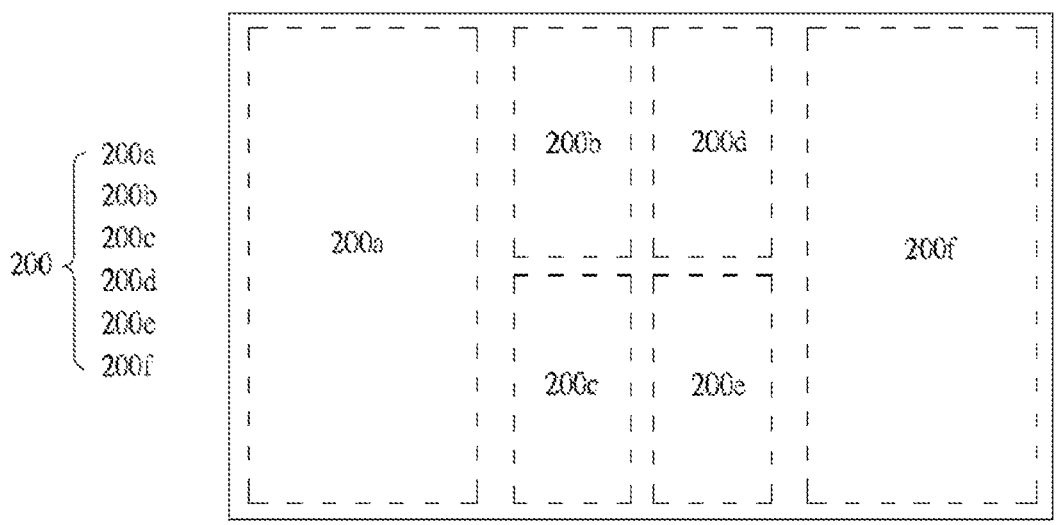
FIG. 5 is a schematic diagram showing a distribution manner of pressure-sensitive sensing zones according to the present invention.

Refer to FIG. 5, which is a schematic diagram showing a distribution manner of the pressure-sensitive sensing zones of the pressure-sensitive sensor pad according to the present invention. The pressure-sensitive sensing zones (200) are distributed on different positions of the pressure-sensitive sensor pad (20) according to arrangement positions of these pierced regions (260). The pressure-sensitive sensing zones are mainly located on the left, middle, and right positions of the pressure-sensitive sensor pad (20), and there exist at least three pressure-sensitive sensing zones (200). According to an embodiment of the present invention, the pressure-sensitive sensing zones (200) may be distributed on the left, middle, and right positions of the pressure-sensitive sensor pad (20) to form six pressure-sensitive sensing zones (200a, 200b, 200c, 200d, 200e, 200f). These pressure-sensitive sensing zones (200) may have the same or different areas, or some of them have the same areas. According to an embodiment of the present invention, the left and right pressure-sensitive sensing zones (200a and 200f) have roughly the same areas, while the four pressure-sensitive sensing zones (200b, 200c, 200d, 200e) distributed in the middle have roughly the same areas. It should be noted that, FIG. 5 only show a preferred embodiment of the pressure-sensitive sensing zones (200) of the present invention, but is not intended to limit their distribution positions, relative positions, and area size.

Furthermore, the pressure-sensitive sensor pad (20) can be placed on the upper cushion or between the upper cushion (12) and the bottom cushion (14). The present invention does not particularly limit the size of the pressure-sensitive sensor pad (20), and the size thereof can be designed or adjusted according to the body type of the patient or the size of the sickbed. In addition, the magnitudes of pressure applied by the patient on the pressure-sensitive sensing zones (200), and pressed parts vary according to whether the patient lies flat or sits on the bed, and/or according to different body types of the patients. In consideration of these facts, the pressure-sensitive sensor pad (20) is designed to have different sizes with reference to the magnitudes of pressure applied on the pressure-sensitive sensing zones (200) and corresponding positions of the pressed parts. For example, in an embodiment of the present invention, a pressure-sensitive sensor pad of 170 cm×90 cm (length×width) may be used, but the present invention is not limited thereto; and a pressure-sensitive sensor pad (20) of another size may also be used.

As described above, for the pressure-sensitive sensor pad (20) that is used for sensing the pressure in a pressure-resistant manner and formed by the upper conductive layer (22), the bottom conductive layer (24), and the insulating layer (26), when the insulating layer (26) deforms under stress, the resistance between the insulating layer (26) and the conductive layers (22 and 24) changes. As such, an electrical signal having a certain relationship with the voltage can be output through a measurement circuit.

Figure 6:
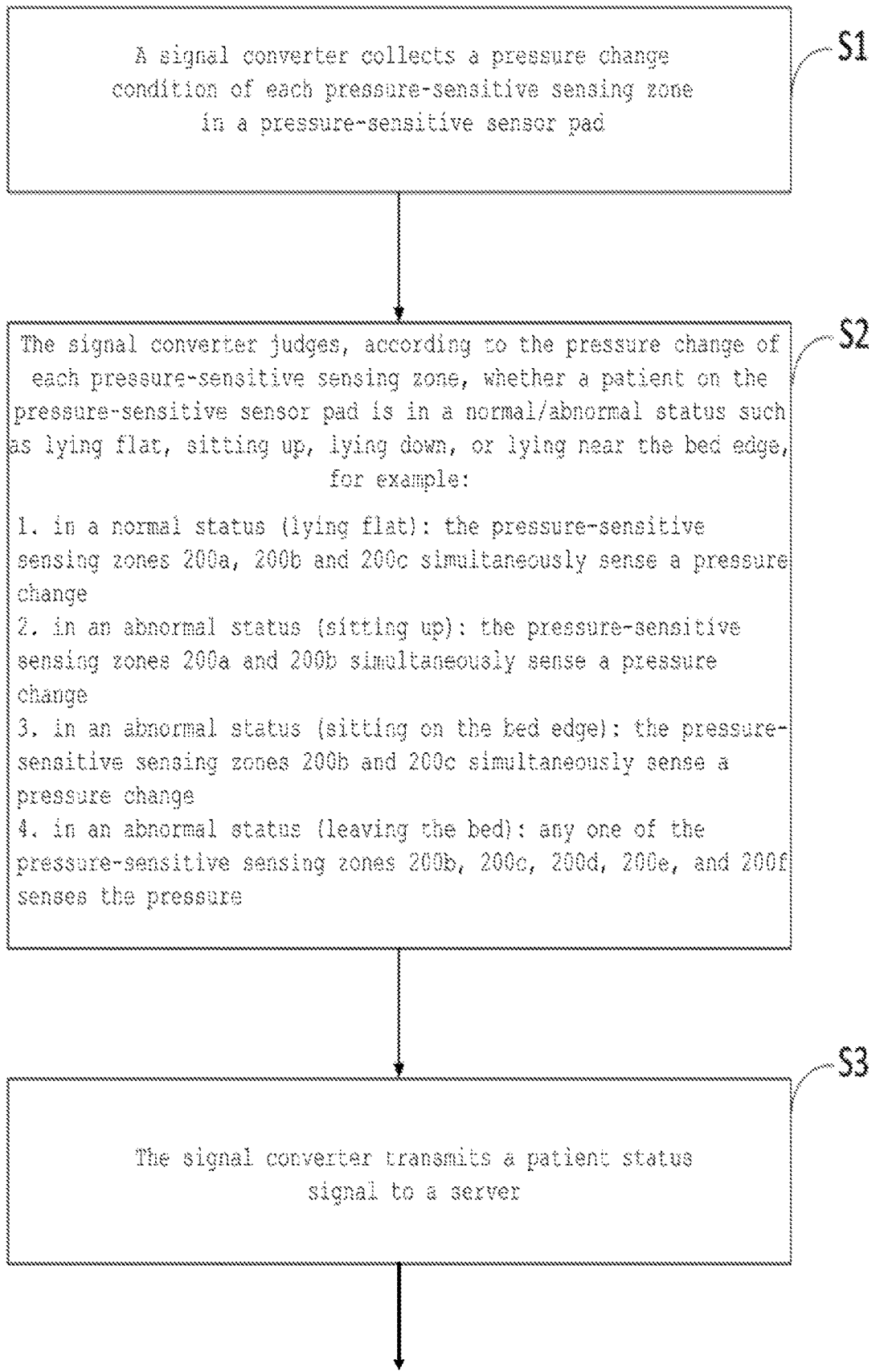
FIG. 6 is a schematic flowchart of operations of a patient off-bed notification system according to the present invention.
Figure 6:
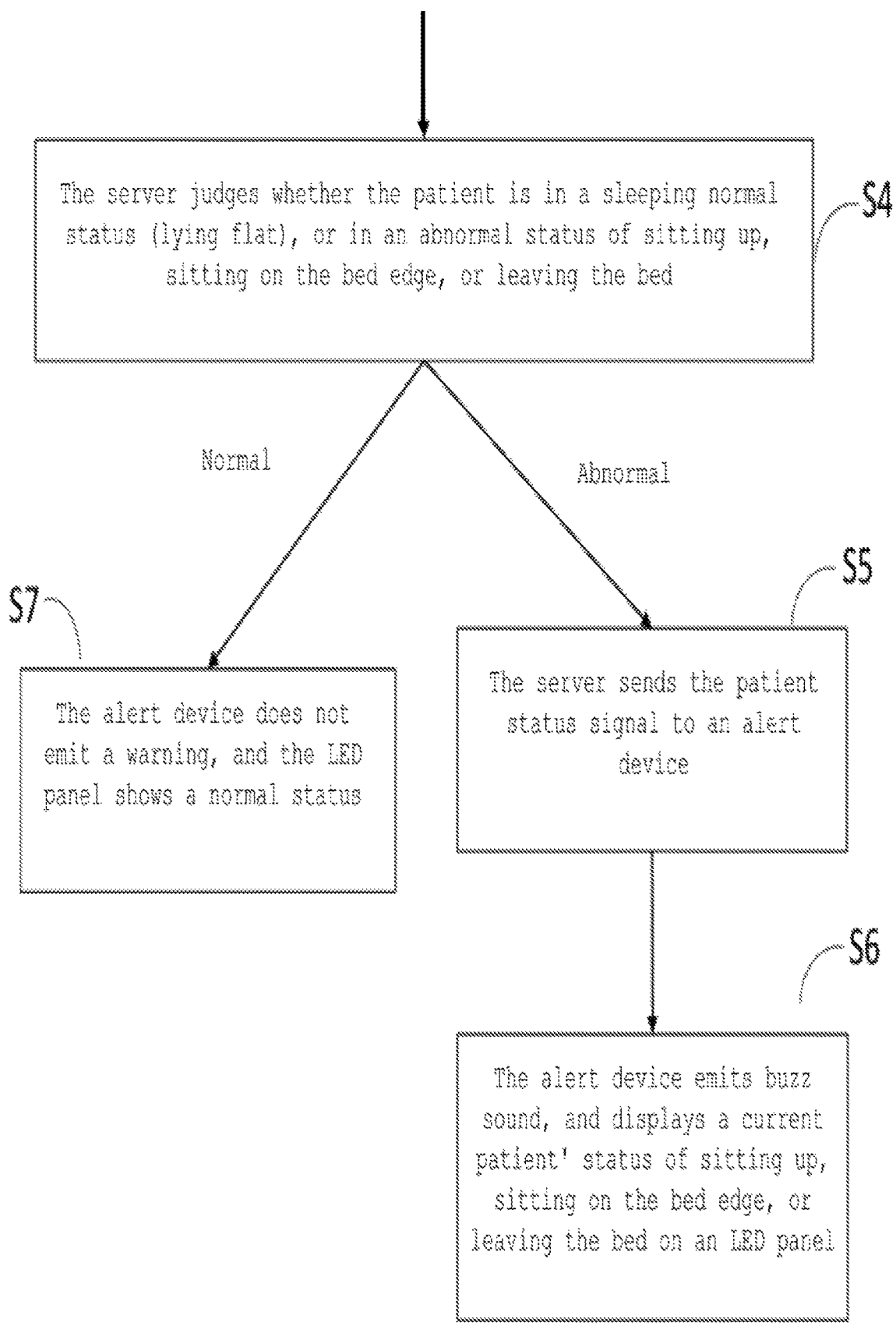

Moreover, refer to FIG. 1, FIG. 2, FIG. 3 and FIG. 4 again, and further refer to FIG. 6 which is a schematic flowchart of operations of a patient off-bed notification system according to the present invention. The signal converter (30) may be formed by an integrated circuit board in which an operation processing chip is embedded. The signal converter is used to collect electrical signals (analog signals) from the pressure-sensitive sensing zones (200) of the pressure-sensitive sensor pad (20); and perform operation processing, analysis, and interpretation. Then, the signal transmitter (40) or the calling device (40') (for example, ZigBee wireless transmission technology with rather low power consumption) sends a patient status signal to a server (50) (for example, a host computer in a hospital nurse station, a desktop computer for home-based care, or a mobile device such as a laptop, a tablet computer or a smart phone) or the monitoring alert apparatus (50'). The server (50) or the monitoring alert apparatus (50') can interpret these signals, record them, and display them on a display unit (51). The display unit (51) may be a computer screen of the host computer or a display screen of a mobile device; or may also be an LED panel connected to the server (50) or the monitoring alert apparatus (50'). In addition, the display unit (51) can also display information that corresponds to a warning signal and includes the position of the bed (10) and symptoms or name of the patient using the bed (10).

As described above, when the patient is in a dangerous status, various alert devices (60) connected to the server (50) or the monitoring alert apparatus (50') via a wireless transmission technology such as WIFI, ZigBee, or Bluetooth are used to receive a signal timely sent by the server (50) or the monitoring alert apparatus (50') and display corresponding information, such that a caregiver can observe the status of the patient at any time. These alert devices (60) display information in different and appropriate visual, auditory, or tactile manners such as light, sound or vibration. For example, the warning signal can be presented in at least one of the following manners: sound, an image, vibration, light, and a digital signal. The alert device may be at least one of a wireless BB call, a mobile phone, a buzzer, an alarm lamp, and an audio alarm; or may also be an alert device having alarm functions of at least two of a buzzer, an alarm lamp, and an audio alarm. Moreover, the server may also display the warning signal on a mobile phone of the caregiver synchronously, such that the caregiver is informed and immediately goes to the ward to find out the patient's status. The following table 1 illustrates statuses of the patient on the bed (10) according to the distribution of the pressure-sensitive sensing zones shown in FIG. 4 of the present invention. In this embodiment, the pressure-sensitive sensing zone 200a is at the position near the head of a patient, and the pressure-sensitive sensing zone 200f is at the position near the feet of the patient.

TABLE 1

| Statuses of the patient | Pressure conditions in different pressure-sensitive sensing zones | | | | | |
|---|---|---|---|---|---|---|
| | 200a | 200b | 200c | 200d | 200e | 200f |
| Sit up | | V | V | | | |
| Sit up | | | | V | V | |
| Sit up | | | | V | V | V |
| Dangerous | | V | | | | |
| Dangerous | | | V | | | |
| Dangerous | | | | V | | |
| Dangerous | | | | | V | |
| Dangerous | | | | | | V |
| Dangerous | | V | V | | | |
| Dangerous | | | V | V | | |
| Dangerous | | | | V | V | |
| Dangerous | | | | | V | V |
| Sleep (lying flat) | V | V | V | | | |

TABLE 1-continued

| Statuses of the patient | Pressure conditions in different pressure-sensitive sensing zones | | | | | |
|---|---|---|---|---|---|---|
| | 200a | 200b | 200c | 200d | 200e | 200f |
| Lie on the bed edge | V | V | | | | |
| Lie on the bed edge | V | | V | | | |

Multiple pressure sensors formed by the pressure-sensitive sensing zones (200) can sense the pressure according to whether there is an external pressure applied thereon, that is, according to the statuses of the patient lying thereon. When the pressure on some of the pressure-sensitive sensing zones (200) increases, the impedance between the upper conductive layer (22) and the bottom conductive layer (24) is reduced and thus the capacitance is changed. Then, the signal transmitter (40) or the calling device (40') sends out an appropriate ZigBee wireless communication signal or wire communication signal. After the pressure-sensitive sensing zones (200) send out corresponding signals according to whether there is a pressure (that is, the weight of the patient) applied thereon, the server (50) or the monitoring alert apparatus (50') comprehensively makes a study according to these signals, to judge whether the patient lies flat, turns over, lies on his/her side, sits up, or sits on the bed edge; or to judge whether the patient intends to leave the bed and whether the leaving time is abnormal. Then, the server sends out a corresponding signal or warning according to a judgment result, such that a user of the alert device can immediately obtain first-hand information, where the information may include the ward number, bed number, patient name, occurrence time of a dangerous condition, and the like.

In this embodiment, the alert device (60) is an alarm having buzzing and lamp warning functions. For example, when the pressure-sensitive sensing zones 200a, 200b and 200c simultaneously sense the pressure, the server (50) or the monitoring alert apparatus (50') judges, according to a patient status signal, that the patient is in a normal flat-lying status. Therefore, it is unnecessary to send out a warning signal, and in this case, the alert device shows a green lamp to indicate a normal status. When the pressure-sensitive sensing zones 200a and 200b simultaneously sense the pressure, the server (50) or the monitoring alert apparatus (50') judges, according to a patient status signal, that the patient is in a dangerous status of lying near the bed edge or sitting on the bed edge. Therefore, the server sends a warning signal to the alert device, and displays patient information on an LED panel of the nurse station. In this case, the alert device shows a warning yellow lamp and emits buzz sound, to indicate that the patient is currently in a dangerous status of lying near the bed edge. After receiving the signal, nursing staff can timely go to the ward to handle the situation. Likewise, when the pressure-sensitive sensing zones 200a and 200c simultaneously sense the pressure, it also indicates that the patient is currently in a dangerous status of lying near the bed edge.

When the pressure-sensitive sensing zones 200b and 200c simultaneously sense the pressure, the server (50) or the monitoring alert apparatus (50') judges, according to a patient status signal, that the patient is in a dangerous status of sitting on the bed. Therefore, the server sends a warning signal to the alert device, and displays patient information on an LED panel of the nurse station. In this case, the alert device shows a warning blue lamp and emits buzz sound, to indicate that the patient is currently in a dangerous status of sitting on the bed. After receiving the signal, nursing staff can timely go to the ward to handle the situation. Likewise, when the pressure-sensitive sensing zones 200d and 200e, or the pressure-sensitive sensing zones 200d, 200e and 200f simultaneously sense the pressure, it also indicates that the patient is currently in a dangerous status of lying near the bed edge.

In addition, when any one of the pressure-sensitive sensing zones 200b, 200c, 200d, 200e and 200f simultaneously senses the pressure, the server (50) or the monitoring alert apparatus (50') judges, according to a patient status signal, that the patient is probably on the point of dropping from the bed or the patient intends to leave the bed, the control terminal sends a warning signal to the alert device, and displays patient information on an LED panel of the nurse station. In this case, the alert device shows a warning red lamp and emits buzz sound, to indicate that the patient is currently in a dangerous status. After receiving the signal, nursing staff can timely go to the ward to handle the situation. Likewise, when the pressure-sensitive sensing zones 200b and 200d, or 200c and 200e, or 200d and 200f, or 200e and 200f simultaneously sense the pressure, it also indicates that the patient is currently in a dangerous status.

Further, if the nursing staff fail to timely handle the situation after receiving the signal indicating that the patient is in a dangerous status, the server (50) or the monitoring alert apparatus (50') may send the corresponding warning signal to the nursing staff holding the alert device at regular intervals, till the nursing staff arrive on site to handle the situation and presses a warning lifting button. The warning lifting button may be configured near the sickbed, on the signal converter, or on the calling device in the ward. After the alarm is lifted, a signal is returned to the server (50) or the monitoring alert apparatus (50'), and then the server (50) stops sending the warning signal and records the warning lifting time.

Further, a few nursing staffs need to take care of multiple patients, or the nursing staff are probably on the move or do not stay on a set position for a long time. Such cases often happen in reality. The present invention uses a ZigBee wireless transmission technology with low power consumption, to design the alert device (60) into a small and portable device, such that the nursing staff can know the patient' status at any time, and thus can timely go to the ward for inspection or give proper assistance.

When the nursing staff need to take charge of a large nursing area, a repeater (not shown in the figure) for receiving patient status signals from pressure-sensitive sensor pads (20) of multiple beds (10) and then transmitting the signals to the alert device (60) may be additionally disposed. Definitely, each alert device (60) may be designed to have both signal sending and receiving functions, that is, each alert device (60) functions as a repeater for the others. Thus, the effective application range of the device can be enlarged, and miss of an important signal can be avoided.

According to the above descriptions and illustrations of the embodiments, it can be confirmed that the patient off-bed notification system disclosed in the present invention can send a signal to inform the caregiver before the patient leaves the bed and notify the caregiver to attend the patient, so that the harm caused when the patient leaves the bed alone can be minimized, thus effectively improving the work efficiency of the caregiver. Further, the patient off-bed notification system disclosed in the present invention can also be connected with calling system of the hospital nurse station directly, which is not only easy to install and use, but also can reduce the installation cost The specific embodiments described above are only used to illustrate the features and effects of the present invention, and are not intended to limit the implementation scope of present invention. Any equivalent changes and modifications made based on the content disclosed in the present invention without departing from the spirit and technical scope of the present invention still fall within the patent scope described later.

What is claimed is:

1. A patient off-bed notification system, comprising:
   a pressure-sensitive sensor pad, comprising an upper conductive layer, a bottom conductive layer and an insulating layer arranged therebetween, wherein the insulating layer comprises a set of pierced regions that partition the pressure-sensitive sensor pad into a plurality of pressure-sensitive sensing zones, wherein the upper conductive layer and the bottom conductive layer is configured to generate an electrical signal due to pressure change at one or more of the plurality of pressure-sensitive sensing zones;
   a signal converter, electrically connected to the pressure-sensitive sensor pad, wherein at least two different pressure-sensing zones of the plurality of pressure-sensing zones generate at least two different electrical signals to the signal converter, wherein the signal converter receives the electrical signals sent by the pressure-sensitive sensor pad and performs operational analysis to produce a corresponding patient status signal, wherein producing the patient status signal comprises (i) identifying, based on the electrical signals, one or more pressure-sensitive sensing zones experiencing the pressure change, (ii) mapping the identified pressure-sensitive sensing zones to a patient status selected from a plurality of defined patient statuses; and
   a signal transmitter, electrically connected to the signal converter, and used to transmit the patient status signal from the signal converter.

2. The patient off-bed notification system of claim 1, wherein the plurality of pressure-sensitive sensing zones have different sensing areas.

3. The patient off-bed notification system of claim 2, wherein the set of pierced regions partition the upper conductive layer, the insulating layer, and the bottom conductive layer.

4. The patient off-bed notification system of claim 1, further comprising a server that is configured to receive the patient status signal sent by the signal transmitter, wherein the server comprises a display unit used to store or display information corresponding to the patient status signal.

5. The patient off-bed notification system of claim 1, further comprising at least one alert device used to send out a warning signal.

6. The patient off-bed notification system of claim 5, wherein the warning signal is presented in at least one of the following manners: sound, an image, vibration, light, and a digital signal.

7. The patient off-bed notification system of claim 5, wherein the at least one alert device is at least one of a wireless BB call, a mobile phone, a buzzer, an alarm lamp, and an audio alarm.

8. The patient off-bed notification system of claim 5, wherein when the patient is in a dangerous status, the alert device unceasingly sends out the warning signal at regular intervals till the dangerous status is lifted.

9. The patient off-bed notification system of claim 1, wherein the signal transmitter wirelessly transmits a WIFI signal.

10. The patient off-bed notification system of claim 1, wherein the pressure-sensitive sensor pad is arranged in a bed that comprises an upper cushion and a bottom cushion, wherein the pressure-sensitive sensor pad is placed on the upper cushion or between the upper cushion and the bottom cushion.

11. The patient off-bed notification system of claim 1, wherein the signal transmitter wirelessly transmits a Bluetooth signal.

12. The patient off-bed notification system of claim 1, wherein the signal transmitter wirelessly transmits a ZigBee signal.

* * * * *